(12) United States Patent
Quan et al.

(10) Patent No.: US 10,821,275 B2
(45) Date of Patent: Nov. 3, 2020

(54) PROTECTIVE RELEASE SHEET FOR MICRONEEDLE PATCH

(71) Applicant: COSMED PHARMACEUTICAL CO., LTD., Kyoto (JP)

(72) Inventors: Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 14/410,300

(22) PCT Filed: Jun. 25, 2013

(86) PCT No.: PCT/JP2013/067387
§ 371 (c)(1),
(2) Date: Dec. 22, 2014

(87) PCT Pub. No.: WO2014/003002
PCT Pub. Date: Jan. 3, 2014

(65) Prior Publication Data
US 2015/0335870 A1  Nov. 26, 2015

(30) Foreign Application Priority Data

Jun. 27, 2012 (JP) ................................ 2012-156948
Aug. 21, 2012 (JP) ................................ 2012-195509

(51) Int. Cl.
*A61M 37/00* (2006.01)
*A61F 13/00* (2006.01)
(Continued)

(52) U.S. Cl.
CPC ..... *A61M 37/0015* (2013.01); *A61F 13/0008* (2013.01); *A61F 13/00076* (2013.01);
(Continued)

(58) Field of Classification Search
CPC ............ A61F 13/0008; A61F 13/00076; A61F 2013/008; A61F 2013/00812; A61F 13/60;
(Continued)

(56) References Cited

U.S. PATENT DOCUMENTS 5,655,654 A * 8/1997 Broskow ............... B65D 71/504
206/150
6,105,579 A * 8/2000 Levitt .................... A61B 19/08
128/849
(Continued)

FOREIGN PATENT DOCUMENTS

CA      1055440 A     5/1979
CA      2155474 A1    2/1996
(Continued)

OTHER PUBLICATIONS

Patent Translate: translation of JP 2010029512 A, Sep. 26, 2014.*
(Continued)

*Primary Examiner* — Nilay J Shah
(74) *Attorney, Agent, or Firm* — Cheng Law Group, PLLC (57) ABSTRACT

Provided is a microneedle patch which is easily to be applied on a skin surface. One or more holes are provided inside a protective sheet of the microneedle patch, and one or more cutting lines running from an outer edge of the protective sheet toward the holes are also provided. The cutting lines may be symmetrically arranged on both sides of the hole. Providing an incision on the outer edge of the cutting lines of the protective release sheet facilitates cutting along the cutting lines. In the use of the microneedle patch, both sides of the cutting line of the protective release sheet are held and torn so as to bring out a microneedle array adhesive sheet and apply it on a skin. Then the microneedle array surface
(Continued)

is slightly compressed, thereby the microneedle is inserted into the stratum corneum.

12 Claims, 6 Drawing Sheets

(51) Int. Cl.
  *A61F 13/60* (2006.01)
  *A61F 13/56* (2006.01)
(52) U.S. Cl.
  CPC .......... *A61F 13/5616* (2013.01); *A61F 13/60* (2013.01); *A61F 2013/008* (2013.01); *A61F 2013/00812* (2013.01); *A61M 2037/003* (2013.01); *A61M 2037/0023* (2013.01); *A61M 2037/0046* (2013.01); *A61M 2209/00* (2013.01); *F04C 2270/0421* (2013.01)
(58) Field of Classification Search
  CPC . A61F 13/5616; A61M 37/015; A61M 37/00; A61M 2037/0023; A61M 2037/003; A61M 2037/0038; A61M 2037/0046; A61M 2037/0053; A61M 2037/0061; A61M 2025/0266; A61M 2025/0273; A61M 5/14248
  See application file for complete search history.

(56) References Cited

U.S. PATENT DOCUMENTS

| | | | |
|---|---|---|---|
| 6,286,511 | B1 | 9/2001 | Levitt et al. |
| 6,334,856 | B1 | 1/2002 | Allen et al. |
| 6,503,231 | B1 | 1/2003 | Prausnitz et al. |
| 6,611,707 | B1 | 8/2003 | Prausnitz et al. |
| 6,623,457 | B1 | 9/2003 | Rosenberg |
| 6,743,211 | B1 | 6/2004 | Prausnitz et al. |
| 7,344,499 | B1 | 3/2008 | Prausnitz et al. |
| 2002/0000232 | A1 | 1/2002 | Levitt et al. |
| 2002/0082543 | A1* | 6/2002 | Park .................... A61B 5/1411 604/21 |
| 2002/0108615 | A1 | 8/2002 | Levitt et al. |
| 2002/0138049 | A1 | 9/2002 | Allen et al. |
| 2003/0199812 | A1 | 10/2003 | Rosenberg |
| 2003/0208167 | A1 | 11/2003 | Prausnitz et al. |
| 2005/0137531 | A1 | 6/2005 | Prausnitz et al. |
| 2006/0047243 | A1 | 3/2006 | Rosenberg |
| 2006/0237338 | A1 | 10/2006 | Nakamae |
| 2007/0083151 | A1* | 4/2007 | Carter ................ A61B 17/205 604/46 |
| 2007/0225676 | A1 | 9/2007 | Prausnitz et al. |
| 2008/0009811 | A1* | 1/2008 | Cantor ................ A61B 17/205 604/272 |
| 2008/0108958 | A1* | 5/2008 | Carter .............. A61M 37/0015 604/272 |
| 2008/0275400 | A1* | 11/2008 | Ferguson .......... A61M 37/0015 604/173 |
| 2008/0287864 | A1 | 11/2008 | Rosenberg |
| 2009/0131905 | A1 | 5/2009 | Allen et al. |
| 2010/0256568 | A1 | 10/2010 | Frederickson et al. |
| 2010/0312191 | A1 | 12/2010 | Allen et al. |
| 2012/0101457 | A1 | 4/2012 | Kato |
| 2013/0072874 | A1 | 3/2013 | Tokumoto et al. |

FOREIGN PATENT DOCUMENTS

| | | |
|---|---|---|
| CA | 2425312 A1 | 4/2002 |
| CA | 2620943 A1 | 3/2007 |
| CA | 2425312 C | 2/2010 |
| CA | 2698632 A1 | 12/2010 |
| CA | 2822428 A1 | 6/2012 |
| CA | 2795995 A1 | 12/2012 |
| CA | 2847711 A1 | 3/2013 |
| CA | 2612005 C | 10/2013 |
| CA | 2589730 C | 3/2014 |
| CA | 2676255 C | 6/2016 |
| CA | 2676221 C | 12/2016 |
| CA | 2769102 C | 9/2017 |
| CA | 2801247 C | 9/2018 |
| CN | 1852845 A | 10/2006 |
| CN | 101208129 A | 6/2008 |
| CN | 201564970 U | 9/2010 |
| CN | 101912663 A | 12/2010 |
| EP | 1 086 718 A1 | 3/2001 |
| EP | 2 759 313 A1 | 7/2014 |
| JP | 2001-149485 A | 6/2001 |
| JP | 2001-517532 A | 10/2001 |
| JP | 2002-517300 A | 6/2002 |
| JP | 2003-238347 A | 8/2003 |
| JP | 2006-69633 A | 3/2006 |
| JP | 2006-345984 A | 12/2006 |
| JP | 2008-522731 A | 7/2008 |
| JP | 3152532 U | 8/2009 |
| JP | 2010-29512 A | 2/2010 |
| JP | 2010029512 A * | 2/2010 |
| JP | 2011-224332 A | 11/2011 |
| KR | 10-2007-0088775 A | 8/2007 |
| WO | WO-99/64580 A1 | 12/1999 |
| WO | WO-00/74763 A2 | 12/2000 |
| WO | WO-2007/002522 A1 | 1/2007 |
| WO | WO-2007/067363 A2 | 6/2007 |
| WO | WO-2011/002034 A1 | 1/2011 |
| WO | WO-2011/148994 A1 | 12/2011 |
| WO | WO-2013/042723 A1 | 3/2013 |

OTHER PUBLICATIONS

International Search Report for the Application No. PCT/JP2013/067387 dated Aug. 13, 2013.
Written Opinion of the International Searching Authority (PCT/ISA/237) for Application No. PCT/JP2013/067387 dated Aug. 13, 2013.
Supplementary European Search Report for the Application No. EP 13 81 0059 dated Feb. 25, 2016.
Written Opinion of the International Searching Authority (PCT/ISA/237) for Application No. PCT/JP2013/067387 dated Aug. 13, 2013 (English Translation dated Jan. 8, 2015).
The First Office Action for the Application No. 201380031586.1 from The State Intellectual Property Office of the People's Republic of China dated Dec. 23, 2015.
Quan, Ying-shu et al., "The Course of Development and Manufacturing for Microneedle", Yakuzaigaku, The Academy of Pharmaceutical Science and Technology, 2009, vol. 69, No. 4, pp. 272-276.
Canadian Office Action for Application No. 2,876,569 dated Nov. 23, 2018.
Korean Office Action for Application No. 10-2014-7035927 dated Nov. 13, 2019.
The First Office Action for the Application No. 201710747653.X from The State Intellectual Property Office of the People's Republic of China dated Oct. 14, 2019.
Notification of Reasons for Refusal for the Application No. 2014-090748 from Japan Patent Office dated Apr. 27, 2018.

* cited by examiner

PROTECTIVE RELEASE SHEET FOR MICRONEEDLE PATCH

TECHNICAL FIELD

The present invention relates to a protective release sheet for a microneedle patch.

BACKGROUND ART

As a method of administering a drug to a human body, an oral administration method and a transdermal administration method are used. Injection is a typical transdermal administration method, but it is painful and likely to cause an infection so that it is not a procedure to be welcome. In contrast, a transdermal administration method without pain using a microneedle array has been recently attracting attention (Patent Document 1, Non-patent Document 1).

Stratum corneum works as a barrier to drug permeation so that only applying a drug on a skin surface cannot cause enough permeability. In contrast, perforation of contemn by using a minute needle, i.e. a microneedle can remarkably improve efficiency in drug permeability compared to that in the application method. It is a microneedle array in which a large number of the microneedles are integrated on a substrate. In addition, a product in which sheets such as an adhesive sheet for adhering the microneedle array to a skin or a protective release sheet for protecting and supporting the adhesive sheet when applying the microneedle array to a skin are added to the microneedle array in order to facilitate its use is called a microneedle patch. Herein, an adhesive sheet means a film, a fabric or a paper to which an adhesive agent is applied.

When a microneedle is produced by using a substance such as a saccharide which dissolves in a body and disappears by metabolism as a material, an accident is not caused even if the needle is broken and remains in a skin. Furthermore, if a drug is contained in the saccharide, the drug can be easily administered into and under the skin by dissolving the inserted microneedle in the body (Patent Document 2).

The protective release sheet is applied on an adhesive face of the microneedle patch. In insertion of the microneedle, a back of the adhesive sheet (a face without adhesive agent) and the protective release sheet are pinched by fingers, and the protective release sheet is peeled off so as to apply the microneedle patch on a skin. The microneedle should not be brought into contact with the fingers during the removal of the protective release sheet.

For the conventional transdermal patch without microneedle, the protective release sheet is usually attached to the whole surface of the adhesive agent. In this process, cutting lines are provided on the protective release sheet, the protective release sheet is hold by a hand, is convexly bent outward and is peeled off so as to apply the transdermal patch on the skin. However, in the case of the conventional microneedle patch, the substrate of the microneedle array was so hard that the patch could not be convexly bent outward, and therefore the patch could not be bent so as to remove the protective release sheet.

PRIOR ART DOCUMENTS

Patent Documents

[Patent Document 1] JP-2002517300A
[Patent Document 2] JP-2003238347A

Non-Patent Documents

[Non-Patent Document 1] Quan Ying-Shu, Kamiyama Fumio, The Course of Development and Manufacturing for Microneedle, Yakuzaigaku; The Academy of Pharmaceutical Science and Technology, Japan; H21-July 69(4), 272-276.

SUMMARY OF THE INVENTION

Technical Problem

Recently, a microneedle array having a flexible substrate has been developed, and ideas for facilitating application of a microneedle patch thereof on a skin have been required. For applying the microneedle patch having the flexible substrate on the skin, a protective release sheet and the back of an adhesive sheet are pinched by fingers, and the protective release sheet is removed from the microneedle patch to apply the patch on the skin. In this step, there is a risk of contamination of the microneedle by bringing the fingers into contact with the adhesive face and the microneedle when removing the protective release sheet.

Solution to Problem

The protective release sheet of the microneedle patch according to the present invention made for solving the above-mentioned problem is characterized by comprising a hole inside and one or more cutting lines running from an outer edge of the protective release sheet to the hole.

The protective release sheet comprises the hole because it is unfavorable that the microneedles is covered by the protective release sheet, and the microneedle patch requires cares different from those required for conventional transdermal patches without microneedles. Preferably, the size of the hole on the protective release sheet is larger than the microneedle patch for preventing damage of the needles of the microneedle patch, and the microneedle array is completely put into the hole.

Since the protective release sheet is placed on the adhesive sheet, the hole thereof is preferably smaller than the adhesive sheet and the protective release sheet covers the peripheral part of the adhesive sheet.

The hole on the protective release sheet can be formed somewhat larger than the microneedle array. There is only the adhesive tape in the interspace between the protective release sheet and the microneedle array, and the width of the interspace is preferably 0.3-3 mm. The presence of the interspace can prevent damage of the microneedle array when removing the protective release sheet. If this interspace is smaller than 0.3 mm, the above-mentioned effect can hardly be achieved, and if it is larger than 3 mm the adhesive tape is bent when the protective release sheet is to be held in a container, and the microneedle array hangs down, resulting in a risk that the microneedles contacts with the container.

A plurality of microneedle arrays can be held by one protective release sheet. In this case, although it is preferable that the sheet has holes as many as the microneedle arrays, a plurality of microneedle arrays may be held in one hole.

In a certain aspect of the present invention, the cutting lines are symmetrically arranged on both sides of the hole.

In addition, the cutting line basically runs between the outer edge of the protective release sheet and the hole, and it does not matter whether it runs linearly or curvilinearly. Typically one hole has two cutting lines, but the number of cutting line may be one or three. The cutting line need not run accurately toward the center of the hole, and it may be arranged in a position or direction somewhat deviated from the center of the hole. Note that it would be better to form a cutting line running from one hole to another hole in some cases.

The cutting line may be a slit which is previously cut off, but it may also be a line with perforated line which can be easily cut off.

An incision may be provided at the cutting line position on the outer edge portion of the protective release sheet. The incision facilitates cutting and removal at the cutting line position. The incision may be linear or curved.

The microneedle of the present invention comprises biosoluble materials like hyaluronic acid and collagen as raw materials, and the length of the microneedle is typically 30-1000 μm. Although the size of the substrate of the microneedle array need not particularly limited, the area of the substrate is typically 0.5-40 cm$^2$, and the thickness of the substrate is 10-2000μ. In addition, it may have various shapes such as circular, oval, comma shape and face-shaped mask.

The protective release sheet prepared by treating one side of the polyester, polyolefin, paper or the like so as to be releasable can be used, and its shape is not limited, but a small hole which is larger than the microneedle patch and smaller than the adhesive sheet should be formed in the center. Desirably, the thickness is 30 to 1,000 μm, preferably 50 to 500 μm. The thickness of less than 30 μm is inconvenient in handling, and the thickness of 1,000 μm or more may be too thick to remove the protective release sheet.

The adhesive sheet of the microneedle patch can be prepared by using polyurethane, polyethylene, polyester, paper or the like as a substrate and applying an acryl- or rubber-based adhesive agent with a thickness of 5-50 μm onto a film with a thickness of 5-50 μm. Although the shape is not particularly limited, it is preferably similar to the shape of the microneedle array, such as circle, oval, comma shape and face shape.

A symbol indicating a position from which the protective release sheet is removed may be provided on one side or both sides of the cutting line of the protective release sheet. As the symbol, arrow is explicit and thus appropriate.

The microneedle patch is housed in a protective case, and then stored and transported as a microneedle patch system. In relation to the protective case, a lidded protective case having a structure that the face of the needles is fixed while kept up from the bottom for protecting the microneedles and preventing their damage should be used. As a specific method for that, the protective release sheet is preferably sandwiched from above and below by first and second case members to support the microneedle patch. Preferably, the protective case is made by thermocompression molding of a polyester sheet.

Advantageous Effects of Invention

Provision of the cutting line to the protective release sheet makes the following possible for applying the microneedle patch to a skin: holding the both sides of the cutting line of the protective release sheet by both hands; bending the microneedle patch convexly outward by one hand; stripping the microneedle patch comprising the adhesive sheet from the protective release sheet; and then applying the microneedle patch easily to the skin. Thereby, accidents such as contact of fingers with the microneedles and contamination of the microneedles can be prevented.

Provision of an interspace between the protective release sheet and the microneedle array can prevent the microneedle array from being torn when the protective release sheet is quickly removed. Thereby, the microneedle patch can be safely handled.

The microneedle patch can be easily handled by providing an incision or an arrow at the cutting line position on the outer edge portion of the protective release sheet. As a result, even a person unfamiliar with handling the microneedle patch can easily apply the microneedle array to the skin.

DESCRIPTION OF EMBODIMENTS

Now, the present invention will be described in detail with reference to the figures, but the present invention should not be limited to the following Examples.

Example 1

Figure 1:
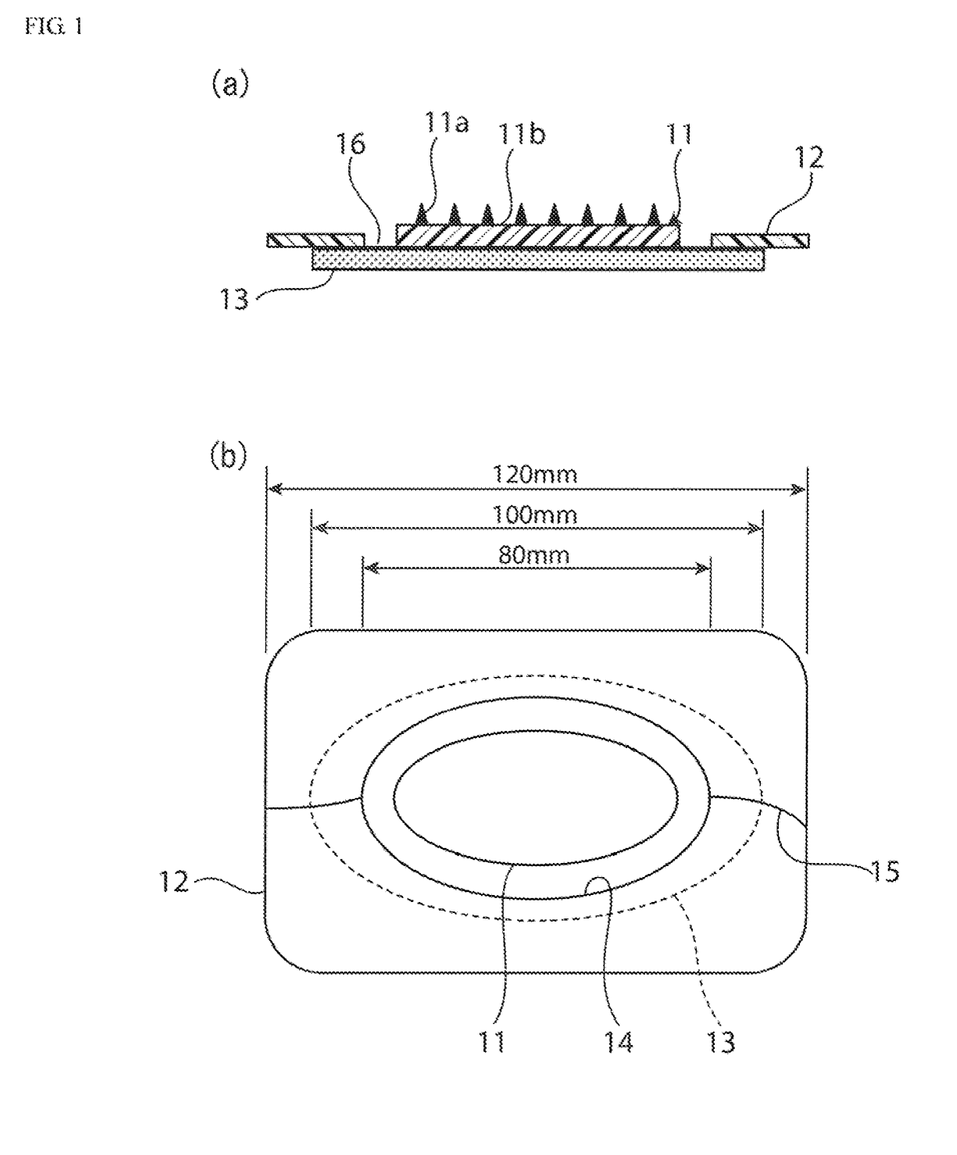
FIG. 1 shows a protective release sheet for one microneedle array. In order to clarify the structure, a sectional view of FIG. 1 (*a*) and a plan view of FIG. 1 (*b*) are illustrated.

The microneedle patch in the present example is shown in FIG. 1. As shown in FIG. 1, a microneedle array 11 has an oval planar shape with a horizontal width of about 65 mm and vertical width of 30 mm. These microneedles 11*a* are placed on a flexible microneedle array substrate 11*b*. Therefore, the entire microneedle array can be deformed according to unevenness of a skin.

Although the size of the microneedle is not limited, 30-1000 μm-long needles are provided at about 50-500 needles/cm$^2$. Although the active ingredient thereof is hyaluronic acid, it may contain components effective in wrinkle reduction for a skin and activation for rejuvenation. In order to clarify the figures, the microneedles are omitted in the plan view of FIG. 1 (*b*), and their number are reduced in the sectional view of FIG. 1 (*a*).

An adhesive sheet 13 is provided on the back of the microneedle array (back side of the paper face in FIG. 1), and has an oval shape slightly larger than that of the microneedle array 11. As shown in the plan view of FIG. 1 (*b*), there is an oval hole in the center part of the adhesive tape, and thus the central part of the microneedle array is not covered with the adhesive tape. The horizontal width of the adhesive tape is 100 mm. Note that the outline of the adhesive tape 13 is drawn by dashed line in the plan view for indicating that it is provided on the back.

A protective release sheet 12 is formed in a rectangular shape with a horizontal width of 120 mm and vertical width of 70 mm and comprises a hole 14 in the center. The hole is larger than the microneedle aria, as shown in the sectional view of FIG. 1 (*a*), an interspace 16 is provided between the microneedle array and the release sheet and a part of the adhesive face of the adhesive tape is exposed. In addition, the protective release sheet is larger than the adhesive sheet and spreads beyond the adhesive sheet.

The cutting lines 15 of the protective release sheet are provided on the right and left sides of the release sheet from its outer edge toward the hole. The protective release sheet is divided into two halves by the cutting lines.

In the use of the microneedle patch, both ends of the protective release sheet 12 between which either of cutting lines runs are held, the protective release sheet is removed from the adhesive sheet along the cutting line, and then the adhesive sheet can be easily removed from the protective release sheet so that the microneedle array 11 can be applied to the skin through the adhesive sheet 13. Subsequently, the surface of the microneedle array 11 is slightly compressed, thereby the microneedle is inserted into the stratum corneum. This insertion hardly causes sensation of pain.

Example 2

Figure 2:
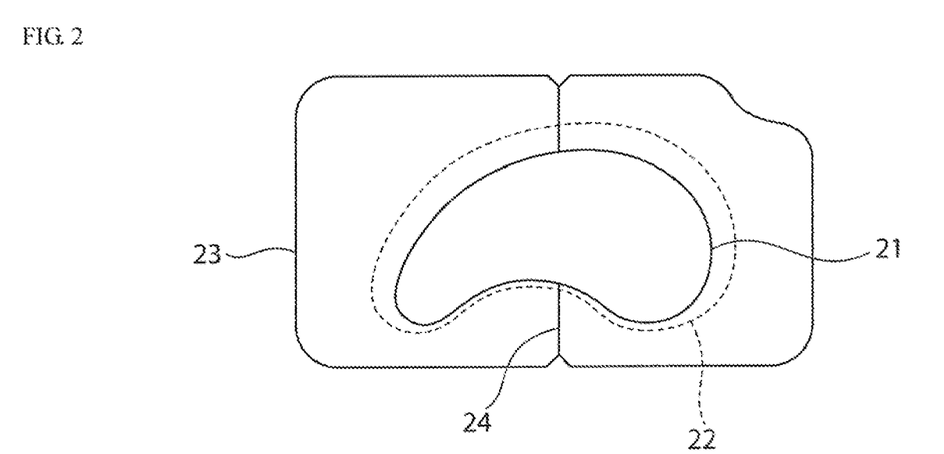
FIG. 2 shows a microneedle patch having a protective release sheet in which cutting lines are provided in a longitudinal direction on the both sides of a microneedle array.

The microneedle patch used in the present example is shown in FIG. 2. The material and usage thereof are the same as in Example 1 except that the microneedle array 21 is formed in a comma shape. In FIG. 2, the surface of the microneedle is drawn as an obverse face, and an adhesive sheet 22 is drawn by dashed line because it is provided on the back of the microneedle array and the protective release sheet. The same goes for Examples 3-9. According to the adhesive sheet 22 of the present example, the width of the bottom part is narrow because the microneedle array of the adhesive sheet is applied as near eyes as possible. A hole on a protective release sheet 23 of the present example is in close contact with the microneedle array 21, and there is no interspace therebetween.

The protective release sheet 23 has cutting lines 24 in a vertical direction, and the cutting lines 24 are symmetrically arranged on both sides of the hole. In addition, a triangular incision is provided in the proximity of the outer edge of the cutting line. This incision facilitates removal of the protective release sheet. Note that the shape of the incision is not limited to the triangular shape and may be an arc shape, an oval arc shape, etc.

The cutting line 24 is provided on the upside and downside in the middle of the protective release sheet 23, so that in the use of this microneedle patch, the both ends of the protective release sheet between which either of cutting lines runs are held, and the adhesive sheet with the microneedle array which was removed while the cutting line of the protective release sheet was broadened such that it was opened is brought into the site to be applied (under the eyes), thereby the patch adheres through the adhesive sheet 22. Subsequently, the surface of the microneedle array 21 is slightly compressed, thereby the microneedle is inserted into the stratum corneum.

Example 3

Figure 3:
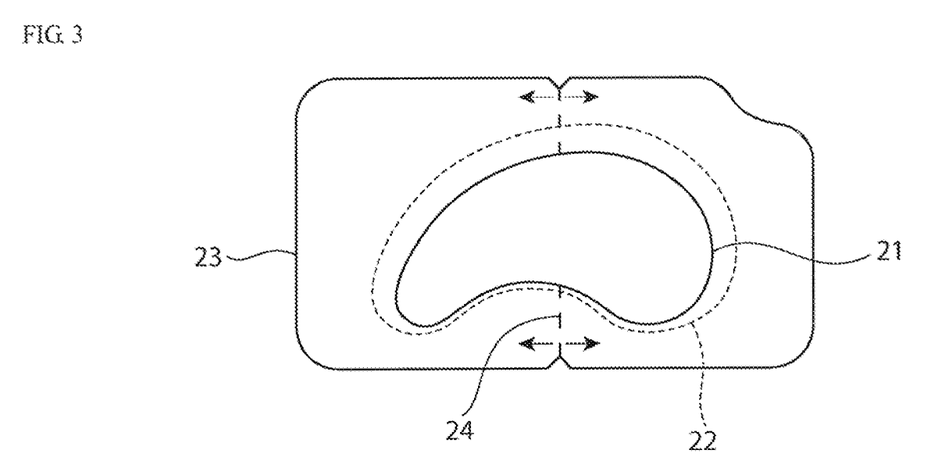
FIG. 3 shows a microneedle patch in which cutting lines of a protective sheet are perforated lines and arrows are provided on the both sides of the cutting line.

In the protective, release sheet of the present example, the cutting lines of the protective release sheet are perforated lines as shown in FIG. 3. If the cutting lines are perforated lines, an accident that the microneedle patch falls by inadvertent cutting of the protective release sheet before application of the microneedle patch can be prevented.

In addition, arrows indicating start positions for removing the protective release sheet are provided on the both side of the cutting lines. Thanks to these arrows, even a user unfamiliar with use of the microneedle patch can easily find the start position for removing the protective release sheet. Note that, the symbol indicating the start position for the removal is not limited to the arrow, and it may be a star sign or the like.

Example 4

Figure 4:
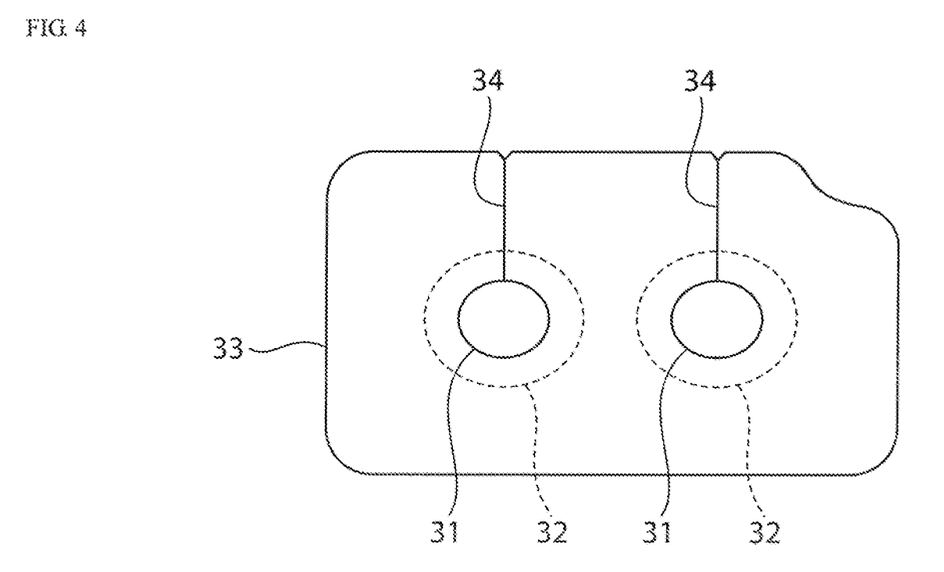
FIG. 4 shows a protective release sheet for two microneedle arrays.

As shown in FIG. 4, the protective release sheet of the present example comprises two circular microneedle arrays 31. Adhesive sheets 32 are provided on the back of the microneedle arrays and the back of a protective release sheet 33, respectively. Each microneedle array comprises one cutting line and can be separately applied to a skin like the microneedle patches in Examples 1-3.

Note that the microneedles are omitted in FIG. 4.

Example 5

Figure 5:
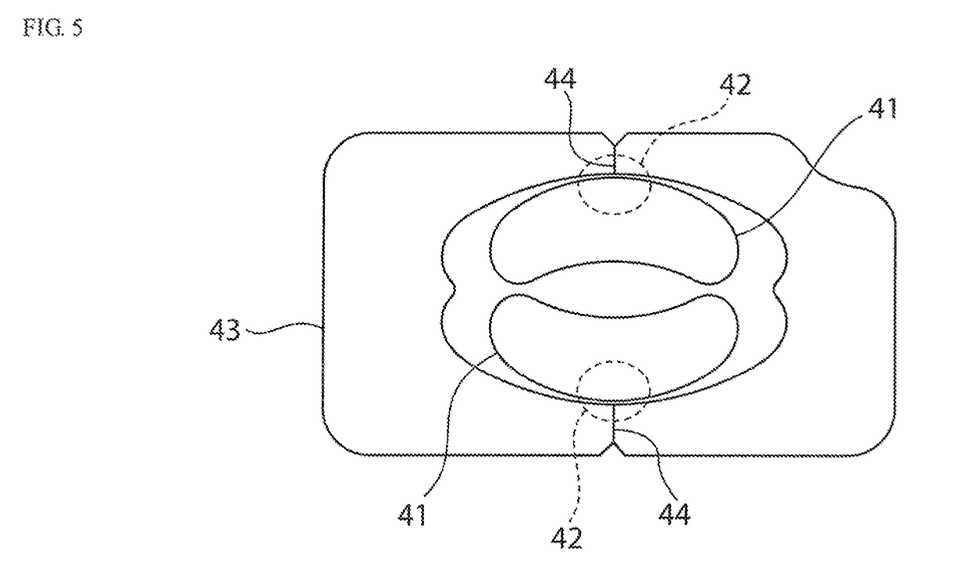
FIG. 5 shows another example of a protective release Sheet for two microneedle arrays.

As shown in FIG. 5, the protective release sheet of the present example has two array-arranged microneedle arrays 41 in one hole. Although each microneedle array comprises an adhesive sheet 42 on its back, this adhesive sheet does not cover the whole back of the microneedle array. Protective release sheet 43 has two cutting lines 44. Each one of patches can be separately applied to a skin like the microneedle patch in Example 4.

Note that the drawing of the microneedles is omitted in FIG. 5.

Example 6

Figure 6:
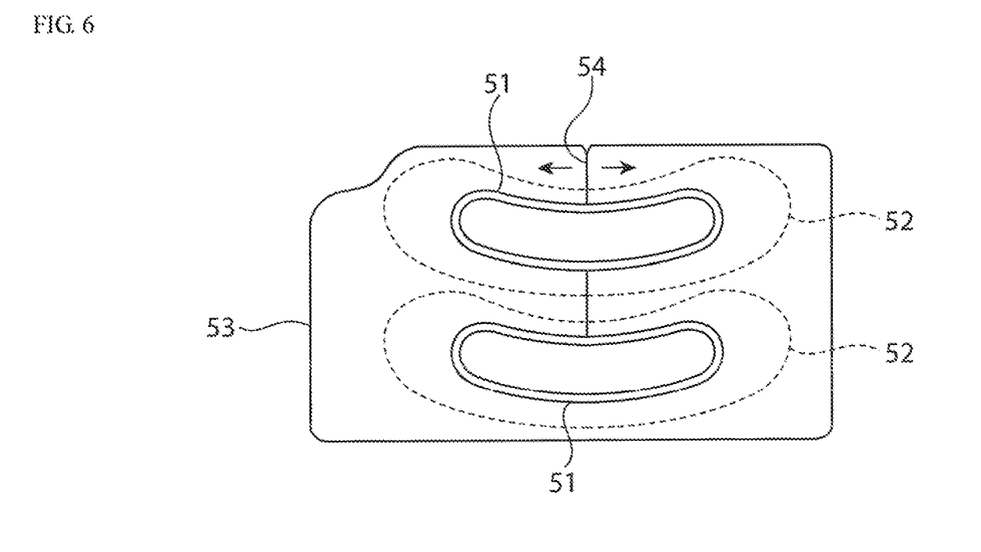
FIG. 6 shows a third example of a protective release sheet for two microneedle arrays.

As shown in FIG. 6, the protective release sheet of the present example has each one of microneedle arrays 51 in two holes. Each microneedle array has an adhesive sheet 52 covering the whole back of the microneedle array on its back. A protective release sheet 53 has two cutting lines 54. Characteristically, one of the two cutting lines runs from the outer edge of the protective release sheet to the upper hole, and another one runs from the upper hole to the lower hole. The hole on this protective release sheet is slightly larger than the microneedle array, and an interspace is provided between the protective release sheet and the microneedle array to facilitate removal of the microneedle patch.

Each one of the patches can be separately applied to a skin like the microneedle patches of Examples 4 and 5. First, the microneedle patch shown in the upper part in FIG. 6 is brought out by cutting the sheet along the cutting line extending from the outer edge, and applied to the skin. Next, the microneedle patch shown in the lower part in FIG. 6 is brought out by cutting the cutting line extending from the upper hole to the lower hole, and applied to the skin.

Example 7

Figure 7:
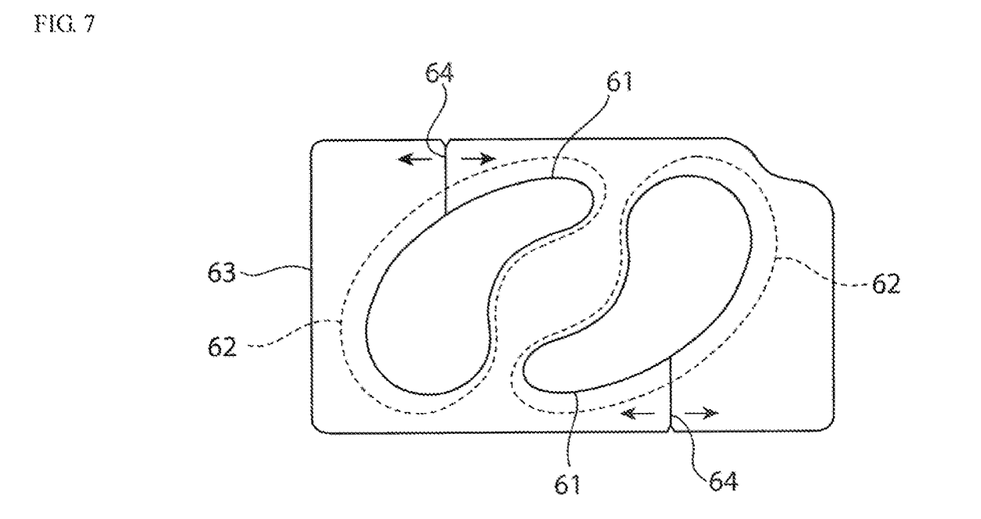
FIG. 7 shows a fourth example of a protective release sheet for two microneedle arrays.

As shown in FIG. 7, the protective release sheet of the present example has each one of comma-shaped microneedle arrays 61 in two holes. Each of the microneedle arrays has an adhesive sheet 62 covering the whole back of the microneedle array on its back. A protective release sheet 63 has two cutting lines 64. Both of the two cutting lines run from the outer edge of the protective release sheet to the holes. Like the microneedle patches of Examples 4-6, the microneedle patch is brought out by cutting the protective release sheet from the cutting line, and then can be separately applied to a skin.

Example 8

Figure 8:
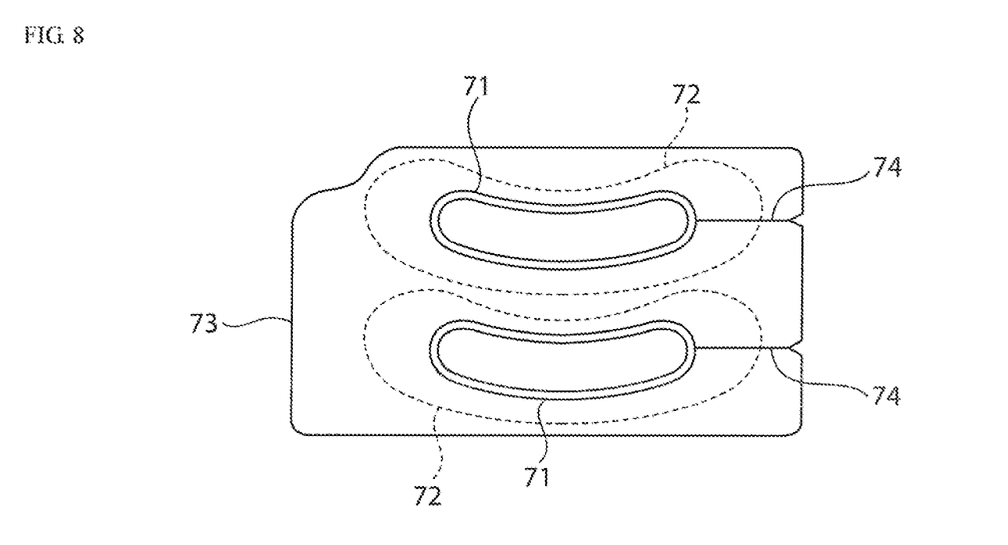
FIG. 8 shows a fifth example of a protective release sheet for two microneedle arrays.

As shown in FIG. 8, the protective release sheet of the present example has each one of microneedle arrays 71 in two holes. Each microneedle array has an adhesive sheet 72 covering the whole back of the microneedle array on its back. A protective release sheet 73 has two cutting lines 74. The positions of the two cutting lines on the protective release sheet are different from those in Example 6. The hole on this protective release sheet is slightly larger than the microneedle array, and an interspace is provided between the protective release sheet and the microneedle array to facilitate removal of the microneedle patch.

Like the microneedle patches of Examples 4-7, the microneedle patch is brought out by cutting the protective release sheet from the cutting line, and then can be separately applied to a skin.

Example 9

Figure 9:
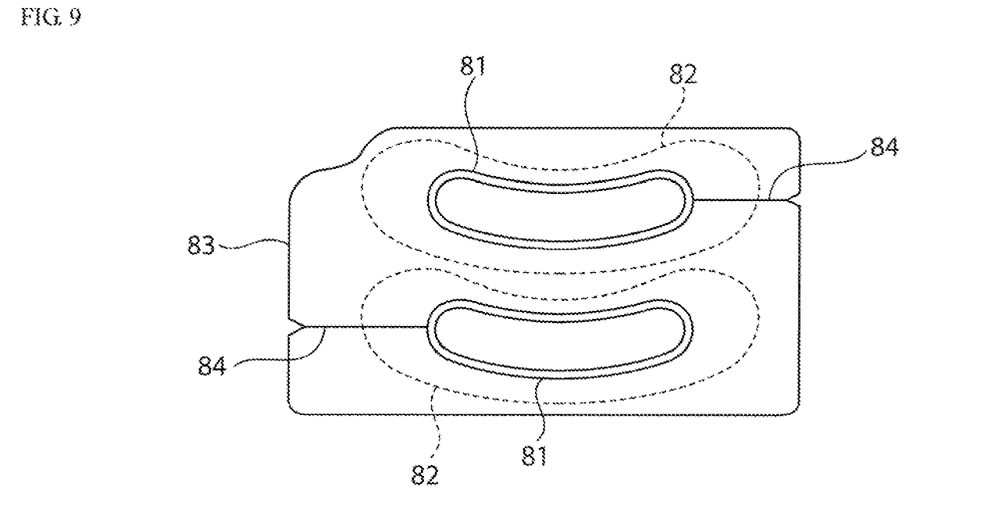
FIG. 9 shows as sixth example of a protective release sheet for two microneedle arrays.
Figure 10:
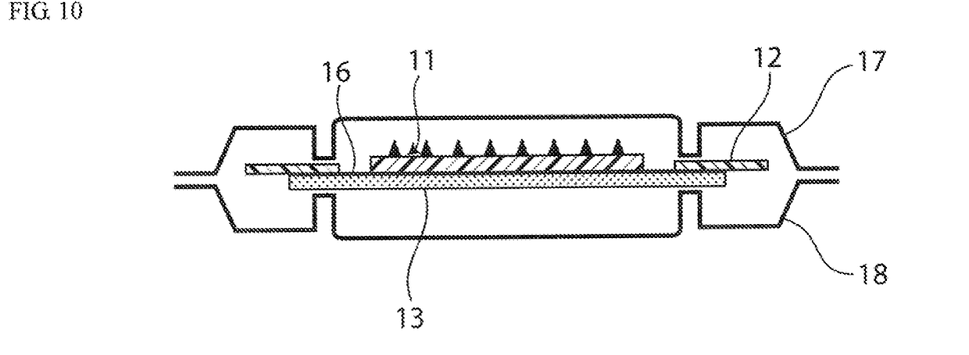
FIG. 10 shows a schematic sectional view in which a microneedle patch is housed in a protective case.

As shown in FIG. 9, the protective release sheet of the present example has each one of microneedle arrays 81 in two holes. Each microneedle array has an adhesive sheet 82 covering the whole back of the microneedle array on its back. A protective release sheet 83 has two cutting lines 84. The positions of the two cutting lines on the protective release sheet are different from those in Examples 6 and 8. The hole on this protective release sheet is slightly larger than the microneedle array, and an interspace is provided between the protective release sheet and the microneedle array to facilitate removal of the microneedle patch.

Like the microneedle patches of Examples 4-8, the microneedle patch is brought out by cutting the protective release sheet from the cutting line, and then can be separately applied to a skin.

The microneedle patch should be handled in a dedicated protective case for preventing contamination and damage of the needles from the fabrication to use. Preferably, the protective case is composed of the microneedle patch and the first and second case members holding the protective release sheet by sandwiching it from above and below. Additionally, the dedicated protective case holds the protective release sheet by sandwiching only the protective release sheet, and must not contact with the needle part of the microneedle patch. In addition, since the patch must be able to be brought out by merely pinching it by fingers in use, the patch is preferably held in such a way that it is kept up from the bottom of the protective case as shown in FIG. 5.

REFERENCE NUMERALS 11, 21, 31, 41, 51, 61, 71, 81 microneedle array
11a microneedle
11b microneedle array substrate
13, 72, 32, 42, 52, 62, 72, 82 adhesive tape
12, 23, 33, 41, 53, 63, 73, 83 protective release sheet
14 hole
15, 24, 34, 44, 54, 64, 74, 84 cutting line
16 interspace
17 first case member
18 second case member

The invention claimed is:

1. A microneedle patch comprising:
   a protective release sheet including a plurality of holes inside and one or more cutting lines running from an outer edge of the protective release sheet to one of the plurality of holes;
   a flexible microneedle array substrate disposed in each hole of the protective release sheet;
   a plurality of microneedle arrays provided on first surfaces of the flexible microneedle array substrates, each microneedle array comprising a plurality of microneedles; and
   a plurality of adhesive sheets adhered to second surfaces of the flexible microneedle array substrates, each adhesive sheet having an adhesive face,
   wherein the second surfaces of the flexible microneedle array substrates are opposite said first surfaces of the flexible microneedle array substrates,
   wherein the adhesive sheets are disposed separately and respectively around the plurality of holes of the protective release sheet,
   wherein the adhesive face of each adhesive sheet extends through and spreads outside of a region corresponding to the flexible microneedle array substrate disposed in the corresponding hole of the protective sheet,
   wherein said protective release sheet has a first surface and a second surface opposed to each other, the first surface of the protective release sheet is adhered to said adhesive sheets, and a thickness of the protective release sheet is less than a thickness of the flexible microneedle array substrates,
   wherein the first surface of the protective release sheet is on the same side of the flexible microneedle array substrates as the second surfaces of the flexible microneedle array substrates in a direction corresponding to the thickness of the flexible microneedle array substrates,
   wherein the protective release sheet spreads beyond the adhesive sheets, and
   wherein each microneedle array is held in the corresponding hole of the protective release sheet.

2. The microneedle patch according to claim 1, wherein: the plurality of holes are formed to provide an interspace between an inner periphery of each hole and the corresponding flexible microneedle array substrate.

3. The microneedle patch according to claim 1, characterized in that an incision is provided on the outer edge of the protective release sheet at a position corresponding to each of the one or more cutting lines running from the outer edge of the protective release sheet to one of the plurality of holes.

4. The microneedle patch according to claim 1, characterized in that there is an even number of the cutting lines, and the cutting lines are symmetrically arranged on both sides of one of the plurality of holes.

5. The microneedle patch according to claim 1, characterized by further comprising an additional cutting line running from one of the plurality of holes to another of the plurality of holes.

6. The microneedle patch according to claim 1, wherein the first surfaces of the flexible microneedle array substrates do not comprise an adhesive sheet.

7. The microneedle patch according to claim 1, wherein said plurality of microneedles of each microneedle array do not pass through the corresponding hole in the protective release sheet.

8. The microneedle patch according to claim 1, wherein a cross-section of at least one microneedle array substrate of the flexible microneedle array substrates has a rectangular shape.

9. The microneedle patch according to claim 1, wherein
the one or more cutting lines are perforated lines, and
symbols indicating start positions for removing the protective release sheet are provided on each side of the one or more cutting lines.

10. The microneedle patch according to claim 1, wherein the first surface of the protective release sheet is planar with at least one of the second surfaces of the flexible microneedle array substrates, and at least one of the flexible microneedle array substrates has a constant thickness.

11. The microneedle patch according to claim 1, wherein each adhesive sheet is prepared by applying an acryl-or rubber-based adhesive agent on a film comprising a material selected from the group consisting of polyurethane, polyethylene, polyester, and paper.

12. The microneedle patch according to claim 11, wherein a thickness of the film is 5-50 μm, and a thickness of the acryl-or rubber-based adhesive agent applied to the film is 5-50 μm.

\* \* \* \* \*